(12) United States Patent
Mercier (10) Patent No.: US 8,637,054 B2
(45) Date of Patent: Jan. 28, 2014

(54) POLYMERIC DELIVERY SYSTEM FOR A NONVISCOUS PROSTAGLANDIN-BASED SOLUTION WITHOUT PRESERVATIVES

(75) Inventor: Fabrice Mercier, Clermont-Ferrand (FR)

(73) Assignee: Laboratoires Thea, Clermont Ferrand (FR)

( * ) Notice: Subject to any disclaimer, the term of this patent is extended or adjusted under 35 U.S.C. 154(b) by 10 days.

(21) Appl. No.: 13/595,165

(22) Filed: Aug. 27, 2012

(65) Prior Publication Data

US 2012/0322871 A1 Dec. 20, 2012

Related U.S. Application Data (63) Continuation of application No. 13/170,716, filed on Jun. 28, 2011.

(60) Provisional application No. 61/359,699, filed on Jun. 29, 2010.

(30) Foreign Application Priority Data

Jun. 29, 2010 (FR) ..................................... 10 55236

(51) Int. Cl.
 *A61K 9/00* (2006.01)
 *A61K 31/557* (2006.01)
(52) U.S. Cl.
 USPC ............................ 424/400; 514/573; 514/913
(58) Field of Classification Search
 USPC .................................. 424/400; 514/573, 913
 See application file for complete search history.

(56) References Cited

U.S. PATENT DOCUMENTS

| | | | |
|---|---|---|---|
| 5,106,615 A | 4/1992 | Dikstein | |
| 6,455,547 B1 * | 9/2002 | Kis | ................................ 514/324 |
| 2002/0103255 A1 * | 8/2002 | Hellberg et al. | .............. 514/530 |
| 2004/0082660 A1 | 4/2004 | Ueno | |
| 2010/0210720 A1 | 8/2010 | Pilotaz et al. | |
| 2011/0319487 A1 | 12/2011 | Mercier | |

FOREIGN PATENT DOCUMENTS

| | | |
|---|---|---|
| EP | 2 127 638 A1 | 12/2009 |
| FR | 2 918 891 A1 | 1/2009 |
| WO | WO 97/29752 A1 | 8/1997 |
| WO | WO 2009/013435 A2 | 1/2009 |

OTHER PUBLICATIONS

Reidmiller et al., Antimicrobial properties of the chelating agent EDTA on STrptococcal bovine mastitis isolates, J Food Prot, Jun. 2006, 69(6), printed from http://www.ncbi.nlm.nih.gov/pubmed/16786875, Abstract only, 1 page.*

Ballal et al., In vitro antimicrobial activity of maleic acid and ethylenediaminetetraacetic acid on endodontic pathogens, Oral Surg Oral Med Oral Pathol Oral Radiol Endod. Nov. 2011;112(5), printed from http://www.ncbi.nlm.nih.gov/pubmed/21872510, Abstract only,2 pages.*

(Continued)

*Primary Examiner* — Gigi Huang
(74) *Attorney, Agent, or Firm* — Wolf, Greenfield & Sacks, P.C.; C. Hunter Baker (57) ABSTRACT

This invention concerns an ophthalmic solution including:
 at least one prostaglandin;
 a solubilizing agent;
 a gelling agent of the carbomer type;
 a carbomer polymerization-inhibiting agent;
 a co-gelling/co-solubilizing agent.

5 Claims, 3 Drawing Sheets

(56) References Cited

OTHER PUBLICATIONS

Kalachandra et al., Lubrication and surface chemical properties of ophthalmic solutions, Ann Ophthalmol. Nov. 1985;17(11), printed from http://www.ncbi.nlm.nih.gov/pubmed/4083661, Abstract only, 1 page.*

Search Report from French Application No. 1055236, dated Nov. 22, 2010.

Brasnu et al., In vitro effects of preservative-free tafluprost and preserved latanoprost, travoprost, and bimatoprost in a conjunctival epithelial cell line. Curr Eye Res. Apr. 2008;33(4):303-12.

Edsman et al., Rheological evaluation and ocular contact time of some carbomer gels for ophthalmic use. Int J Pharm. 1996;137:233-241.

McCarey et al., In vivo corneal epithelial permeability following treatment with prostaglandin analogs [correction of analoges] with or without benzalkonium chloride. J Ocul Pharmacol Ther. Oct. 2007;23(5):445-51.

Thimons, The New Class of Ophthalmic Agents: Here's how to choose the right prostaglandin for the each patient. Optometric Management. May 2002. Last accessed on Nov. 7, 2011 available at http://www.optometric.com/printarticle.aspx?article=70441. 4 pages.

International Search Report and Written Opinion for PCT/EP2011/060848, mailed Aug. 5, 2011.

International Preliminary Report on Patentability for PCT/EP2011/060848, mailed Oct. 25, 2012.

* cited by examiner

Figure 2C

POLYMERIC DELIVERY SYSTEM FOR A NONVISCOUS PROSTAGLANDIN-BASED SOLUTION WITHOUT PRESERVATIVES

RELATED APPLICATIONS

The present application is a continuation of and claims priority under 35 U.S.C. §120 to U.S. patent application, U.S. Ser. No. 13/170,716, filed Jun. 28, 2011, which claims priority under 35 U.S.C. §119(a) to French application no. 1055236, filed Jun. 29, 2010, and claims priority under 35 U.S.C. §119(e) to U.S. provisional application, U.S. Ser. No. 61/359,699, filed Jun. 29, 2010, each of which is incorporated herein by reference.

FIELD OF THE INVENTION

The invention concerns eye drops or an ophthalmic solution whose active ingredient includes at least one prostaglandin, said solution containing no antimicrobial agents, notably of the quaternary ammonium type (such as benzalkonium chloride [BAK]).

More precisely, and in the context of the invention, a polymeric delivery system has been developed to allow the prostaglandin solution to be as effective as a solution containing BAK, but without the disadvantages from a toxicological and allergenic point of view.

BACKGROUND OF THE INVENTION

Prostaglandins are well-known active ingredients administered topically to humans or animals in the form of eye drops for the treatment of glaucoma. The usual dosage of these formulas is 1 drop a day in each eye, it being understood that prostaglandins can also be used in combination with a second antiglaucoma agent such as, for example, beta blockers, carbonic anhydrase inhibitors or alpha-adrenergic agonists.

The first disadvantage of prostaglandins is that they are not water-soluble, meaning that they require a solubilization step before including them in the eye drop solution.

Furthermore, another constraint for the formulator is to propose an ophthalmic solution that is chemically stable over time at ambient temperature, in practice over a period of 18 to 24 months. Another characteristic required of the ophthalmic solution is that it should remain stable in relation to the packaging in which it is stored, notably plastic packaging such as low-density polyethylene (LDPE).

One last constraint that can arise is avoiding contamination of the ophthalmic solution by antimicrobial agents, notably in multi-dose packaging. This problem can be solved, however, using single-dose unit packaging or a specialized system for this (ABAK® or COMOD® systems, for example).

Thus, to date, most prostaglandin-based ophthalmic solutions on the market include a preservative which, beyond its antimicrobial properties, also ensures solubilization of the active ingredient and, partially, its stabilization. An example of this is the product sold by Pfizer under the Xalatan® brand, which combines latanoprost and BAK at 0.02% by weight. It should be pointed out that, despite the presence of BAK, these eye drops are not stable at ambient temperature and must be stored cold, at a temperature of approximately 5° C. Furthermore, the Allergan company sells eye drops under the Lumigan® brand, combining bimatoprost and BAK at 0.005% by weight.

However, many publications discourage the use of antimicrobial preservatives, and particularly BAK, for long-term treatments in ophthalmology, as is notably the case of glaucoma, due to tolerance problems (on this subject, see "The New Class of Ophthalmic Agents: Here's how to choose the right prostaglandin for the each patient" by J. James Thimons, O.D., F.A.A.O.—Optometric Management, May 2002).

It thus has now been established that antimicrobial preservatives are toxic in long-term use, to such an extent that today there is a tendency to limit their use by reducing their concentration as much as possible in eye drops or, even better, to eliminate them completely from the formulas.

This problem was taken into account in document WO 97/29752, for example, which discloses the use of a non-ionic agent of the Cremophor® type instead of BAK. In the proposed formula, the BAK concentration is limited to 0.01% by weight, the concentration of Cremophor® EL being 0.05% by weight. A product sold by Alcon, called Travatan®, can be found on the market, combining Travoprost, BAK and Cremophor®.

Polysorbate 80 has also been proposed in ophthalmic solutions to partially reduce the concentration of BAK, as is the case, for example, of the product sold by Novartis under the Rescula® brand, combining unoprostone with a mixture of BAK and polysorbate 80 at 0.015% by weight of the solution.

On the other hand, document US2004/0082660 describes an ophthalmic solution with no BAK and containing a mixture of latanoprost and polysorbate 80.

The problem that the invention proposes to solve is therefore that of developing a prostaglandin-based formula that meets at least the following conditions:
  it contains no antimicrobial preservatives;
  it is stable over time in a solution at ambient temperature (18 to 24 months, as a minimum);
  it is compatible with the plastic packaging in which it is usually stored, notably LDPE packaging;
  it is practically as effective in terms of reducing intraocular pressure (IOP) as products available with a BAK base.

Another objective is to propose a formulation that is sufficiently fluid to be packaged using an aseptic packaging technique such as "Blow-Fill-Seal" (single-dose unit).

DESCRIPTION OF THE INVENTION

The Applicant has developed a new delivery system enabling prostaglandin to act with the same effectiveness as that reported with BAK.

Beyond its preservative role, BAK, and more generally quaternary ammonium molecules, have a so-called "soap" effect providing greater penetration by the active ingredient molecules into the eye tissue, but on the other hand they have a toxic effect (irritation, ocular dryness, inflammation, etc.). The delivery system developed in the invention therefore provides equivalent penetration and activity using a different mechanism of action. In any case, it does not have the disadvantages of the conventional preservatives of the BAK type.

More precisely, this invention concerns an ophthalmic solution including:
  at least one prostaglandin;
  a solubilizing agent;
  a gelling agent of the carbomer type;
  a carbomer polymerization-inhibiting agent;
  a co-gelling/co-solubilizing agent.

As mentioned above, such a solution advantageously contains no antimicrobial preservatives, advantageously of the quaternary ammonium type, and even more advantageously benzalkonium chloride (BAK).

In the rest of the description, "antimicrobial preservative" designates a preservative with antimicrobial properties, i.e. a compound capable of protecting the ophthalmic solution from possible microbial contamination. Such a preservative as meant in the invention is to be distinguished from preservatives acting on the solution's chemical preservation, for example antioxidants such as EDTA.

The solution claimed contains at least one prostaglandin as its active ingredient. In practice, there is at least one prostaglandin in the solution and these are chosen from the group including 17-phenyl-13,14 dihydro trinor prostaglandin $F_{2\alpha}$ isopropyl ester (latanoprost), 20-ethyl prostaglandin $F_{2\alpha}$, (+)-fluprostenol isopropyl ester (travoprost), 17-phenyl trinor prostaglandin $F_{2\alpha}$ amide, 17-phenyl-13,14 dihydro trinor prostaglandin $F_{2\alpha}$ ethyl amide (bimatoprost), tafluprost prostaglandin $F_{2\alpha}$ ethanolamide, bimatoprost (free acid)-$d_4$, bimatoprost-$d_4$, latanoprost ethyl amide, 13,14 dihydro-15-keto-20-ethyl prostaglandin $F_{2\alpha}$ (unoprostone), 13,14 dihydro-15-keto-20-ethyl prostaglandin $F_{2\alpha}$ isopropyl ester (unoprostone isopropyl ester). Advantageously, latanoprost is used.

According to another characteristic, the concentration of prostaglandin in the solution is between 0.002 and 0.15% (w/v).

Conventionally, the prostaglandin(s) can be combined with a second active ingredient, notably with other classes of antiglaucoma agents so they can thus work synergistically. For example, these may include beta blockers chosen from the group including timolol maleate and carteolol chloride, carbonic anhydrase inhibitors such as those, for example, chosen from the group including dorzolamide chloride, or alpha-adrenergic agonist such as, for example, brimonidine tartrate. Examples of combinations of prostaglandins and beta blockers include, for example:

Xalacom®—Pfizer: Latanoprost 0.005%+Timolol 0.5%,
Ganfort®—Allergan: Bimatoprost 0.03%+Timolol 0.5%
DuoTrav®—Alcon: Travoprost 0.004%+Timolol 0.5%.

In practice, the antiglaucoma agent accounts for between 0.1 and 0.5% (w/v) of the solution.

As indicated above, such a solution requires the presence of a so-called solubilizing agent capable of solubilizing the prostaglandin(s). This solubilizing agent, preferably non-ionic, advantageously has surface-active properties. Ideally, this would be macrogolglycerol hydroxystearate (hydrogenated ethoxylated castor oil or PEG-40 Hydrogenated Castor Oil; CAS number 61788-85-0). Another potential candidate is polyoxyl 15 hydroxystearate or macrogol 15 hydroxystearate (CAS number 70142-34-6), or polysorbate 20 (CAS number 9005-64-5), or polysorbate 60 (CAS number 9005-67-8) or polysorbate 80 (CAS number 9005-65-6). The concentration of the solubilizing agent in the solution is typically between 0.1 and 20% (w/v), advantageously between 0.5 and 5% (w/v).

Another important characteristic of the ophthalmic solution is its viscosity. This is advantageously between 8 and 20 mPa·s (cP), even more advantageously between 10 and 14 mPa·s (cP), when measured with a Brookfield RVDV III rotational viscometer at 25° C. This solution can indeed be distinguished from an aqueous gel, typically characterized by a viscosity between 400 and 800 mPa·s (cP) and which constitutes a long-acting form to obtain sustained release of the active ingredient.

This invention is based on the development of a suitable gelling system, based on the combination of two gelling agents to obtain a nonviscous polymeric delivery system:
  a first gelling agent, a carbomer in this case, normally suitable for polymerizing and forming a gel but whose polymerization, expansion or maintenance in gel form is inhibited by a so-called breaking agent. Said agent inhibits the polymerization of the carbomer and can be a source of sodium ions, advantageously sodium EDTA, sodium acetate or sodium chloride. Alternatively, it can be a polyol with a low molecular weight such as glycerol (see FR 2 604 906). Furthermore, the carbomer is present in the solution at controlled concentrations, advantageously between 0.05 and 0.2% (w/v). Obviously, the relative concentration of the inhibiting agent is also important: between 0.01 and 1% (w/v) in the case of sodium ions, for example 0.02 to 0.1% for sodium EDTA or 0.5 to 3% (w/v) in the case of polyols, for example glycerol;
  a second agent, called a co-gelling/co-solubilizing agent, is used to ensure the desired level of viscosity and to potentiate the solubilization of the active ingredient, prostaglandin. This is typically a polymer such as polyethylene glycol (PEG) or vinyl derivatives such as polyvinyl alcohol (PVA) or polyvinylpyrrolidone (PVP). Advantageously, its concentration is between 0.5 and 2.5% (w/v).

In the frame of the present invention, a carbomer is defined according to the European Parmacopoeia, i.e. "a cross-linked polymer of acrylic acid of very high relative molecular mass, comprising a large proportion of carboxylic groups" and by its CAS number 9003-01-4. There are several grades of carbomers which can be used in the invention: 910/934/934P/940/941/971 and 974P, advantageously 974P.

In the frame of the present invention, PEG or macrogol is defined according to the European Parmacopoeia, i.e. "a mixture of polymers with the general formula H—(OCH$_2$—CH$_2$)n-OH where n represents the average number of oxyethylene groups". The type of macrogol is defined by a number that indicates the average relative molecular mass. More advantageously, PEG 4000 having CAS number 25322-68-3 is used.

Of course, the composition of the invention may contain the usual additives excluding antimicrobial preservatives. These may include, for example, non-ionic ionizing agents such as polyols (sorbitol, for example). They may also be antioxidants or buffer systems (for example, sodium hydroxide as a neutralizing agent).

According to a preferred embodiment, the claimed composition is made of the ingredients listed in the table below, advantageously in the mentioned amounts:

| PRODUCTS | FUNCTION | CENTESIMAL FORMULA (g/100 ml) |
| --- | --- | --- |
| Carbomer 974 P | gelling agent | 0.10 |
| Sorbitol | isotonic agent | 3.50 |
| PEG 4000 | co-gelling/co-solubilizing agent | 1 |
| EDTA | Na+ ion source | 0.05 |
| sodium hydroxide | Neutralizing agent | qs pH = 7.0 |
| Prostaglandine F2α | Active ingredient | 0.005 |
| Macrogol glycerol hydroxystearate 40 | solubilizing agent | 5.0 |
| water | vehicle | qsp 100 ml |

The formulation of the invention can be presented in single-use (single-dose unit) bottles or in multi-dose bottles, for example Abak® or Comod® or the equivalent, such bottles allowing the eye drops to be applied over several days without preservatives.

The subject of the invention is thus a single-use (single-dose unit) or multi-dose bottle containing the ophthalmic solution described above, made of EP-quality LDPE containing no additives.

Indeed, the solution's fluidity, combined with the product's stability when packaged in a LDPE container, makes its production compatible with BFS technology.

Furthermore, the solution according to the invention is stable for at least 18 months, or even at least 24 months, at ambient temperature (25° C.-30° C.).

Of course, the invention also concerns the use of the ophthalmic solution as described above in the production of a medicine to treat glaucoma in humans or animals, notably its capacity to reduce intraocular pressure and/or provide neuroprotection to the retinal tissue.

Thus, in this context, it has been demonstrated that this delivery system is less aggressive to eye tissue than the solubilization systems in the prior art, insofar as the reduction in intraocular pressure is more regular and linear after administration of the solution.

In practice, the eye drops are administered at a dose of one drop a day in each eye.

The invention also concerns a therapeutic treatment method for glaucoma in humans or animals consisting in instilling the previously described ophthalmic solution at a dose of one drop a day in each eye.

The present application reveals that contrary to the technical solutions disclosed in the prior art, administering a composition according to the present invention leads to a regular and progressive decrease of the intra-ocular pressure (IOP), without an intermediary initial IOP increase. Thanks the present composition, the IOP decrease starts earlier, with an end-effect at least equal possibly better. Without being bound to a theory, this effect on IOP could be due to the presence of the delivery system able to counteract or at least to attenuate the agressivity of the solubilizing agent. Moreover, a composition according to the invention is safe and well-tolerated.

The invention and the resulting advantages will become more apparent with the following embodiments supported by the appended figure.

BRIEF DESCRIPTION OF DRAWINGS

FIG. 2 reports clinical data concerning the tolerability of EXAMPLE 1 composition versus Xalatan®: A/ocular subjective symptoms score upon instillation; B/ocular subjective symptoms not upon instillation; C/overall conjunctival hyperaemia.

I/COMPOSITIONS ACCORDING THE PRESENT INVENTION

1a/Example 1 Composition

| PRODUCTS | CENTESIMAL FORMULA (g/100 ml) |
|---|---|
| Carbomer/gelling agent | 0.10 g |
| Sorbitol/isotonic agent | 3.50 g |
| PEG/co-gelling/co-solubilizing agent | 1.00 g |
| EDTA/Na+ ion source | 0.05 g |
| 1N sodium hydroxide/Neutralizing agent | qs pH = 7.0 |
| Latanoprost/Active ingredient | 0.005 g |
| Macrogol glycerol hydroxystearate 40/solubilizing agent | 5.00 g |
| WFI-grade water/Vehicle | qs 100 ml |

1b/Example 2 Composition

| PRODUCTS | CENTESIMAL FORMULA (g/100 ml) |
|---|---|
| Carbomer/gelling agent | 0.10 g |
| Sorbitol/isotonic agent | 3.50 g |
| PVP/co-gelling/co-solubilizing agent | 2.00 g |
| Sodium acetate/Na+ ion source | 0.8 g |
| 1N sodium hydroxide/Neutralizing agent | qs pH = 7.0 |
| Latanoprost/Active ingredient | 0.005 g |
| Macrogol glycerol hydroxystearate 40/solubilizing agent | 5.00 g |
| WFI-grade water/Vehicle | qs 100 ml |

1c/Example 3 Composition

| PRODUCTS | CENTESIMAL FORMULA (g/100 ml) |
|---|---|
| Carbomer/gelling agent | 0.15 g |
| Sorbitol/isotonic agent | 2.25 g |
| PVA/co-gelling/co-solubilizing agent | 0.50 g |
| Sodium chloride/Na+ ion source | 0.25 g |
| 1N sodium hydroxide/Neutralizing agent | qs pH = 7.0 |
| Travoprost/Active ingredient | 0.004 g |
| Macrogol 15 hydroxystearate/solubilizing agent | 0.50 g |
| WFI-grade water/Vehicle | qs 100 ml |

2/CHARACTERIZATION OF THE EXAMPLE 1 FORMULATION

The solution obtained is opalescent, free of visible particles, with pH between 6.6 and 7.2 (pH-neutral formulation) and osmolality between 270 and 340 mosmol/kg (isotonic formulation).

The solution's viscosity, measured with a Brookfield rotational viscometer (Mobile no. 00/UL measurement chamber), is between 8.0 and 14.0 mPa·s at 25° C.

Furthermore, the solution has been demonstrated to be stable for at least 24 months at ambient temperature (25 or 30° C.).

3/EFFECTIVENESS OF THE EXAMPLE 1 COMPOSITION: EVALUATION OF EFFECTIVENESS IN REDUCING INTRAOCULAR PRESSURE AFTER ADMINISTRATION TO THE EVES OF NORMOTENSIVE ALBINO RATS

The effects of the eye drops in the EXAMPLE 1 formulation on intraocular pressure were evaluated in normotensive rats, compared with clinically available eye drops, i.e. Xalatan®, each product containing latanoprost at a concentration of 0.005% Importantly, Xalatan® contains the antimicrobial agent benzalkonium chloride (BAK), whereas the EXAMPLE 1 formulation does not.

Sixteen male albino rats (Wistar) were involved in this study. They were distributed into 2 groups of 8 animals each, dedicated to the EXAMPLE 1 formulation and to the reference product, Xalatan®, respectively. All the animals were treated in the right eye with 4 instillations of 10 µl each, once every 2 min, for a total of 2 µg of latanoprost. Intraocular pressure (IOP) was measured using the "Tonolab rebound tonometer" system on both eyes 1 hour, 2 hours, 4 hours, 6 hours and 8 hours after administration.

Figure 1:
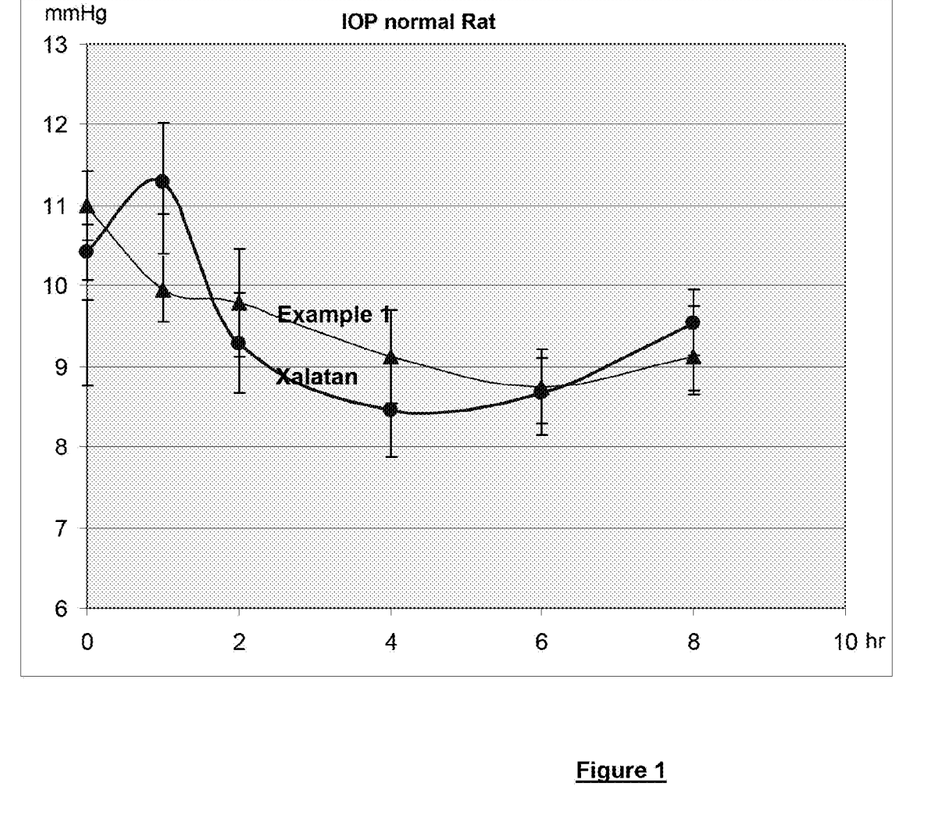
FIG. 1 illustrates the effects of 2 eye drop formulations containing 0.005% latanoprost (EXAMPLE 1 composition indicated by full triangles and Xalatan® indicated by full circles) on intraocular pressure (IOP) in rats.

The results of this study are shown in FIG. 1. In the Wistar rat, the dose of Xalatan® administered produced a biphasic change in IOP, i.e. an increase in the initial pressure (+11.4%), with a peak at 1 hour, followed by a prolonged hypotensive response from 2 to 8 hours after treatment, with an IOP reduction peak at t=4 hours (−18.4%). The same dose (2 μg) of latanoprost in the EXAMPLE 1 formulation reduced the IOP constantly and progressively, achieving a 16% reduction at t=4 hours after topical administration. This effect lasted for 4 to 8 hours, with a maximum IOP reduction peak (−20%) at t=6 hours.

In conclusion, it should be pointed out that:
there is an early hypertension phase that is present with Xalatan® but does not exist with the EXAMPLE 1 formulation in normotensive rats;
the EXAMPLE 1 formulation brought about a reduction in IOP that is relatively similar to that observed with the clinically available reference product, i.e. Xalatan®;
the absence of BAK in the EXAMPLE 1 solution does not compromise its effect on the reduction of IOP.

4/OCULAR TOLERANCE TO THE EXAMPLE 1 COMPOSITION

Ocular tolerance to the EXAMPLE 1 product compared with Xalatan® was tested at 28 days with two instillations a day (50 μl) in pigmented rabbits.

The study gave the following results:
In terms of general tolerance, all the animals presented normal development in terms of body weight, good health and no particular symptoms. Water and food consumption were also normal.
In terms of ocular tolerance, administration of the EXAMPLE 1 product did not cause any ocular effects except a slight, transitory redness in 1 animal out of 10. Xalatan® did not cause any ocular effects except for a slight, transitory redness in 2 animals out of 10. Whatever the treatment, cornea coloring was observed in some animals:
1. EXAMPLE 1: slight to moderate for 6 animals out of 10;
2. Xalatan®: slight for 4 animals out of 10;
3. Control group: slight to moderate for 7 animals out of 10.
This ocular effect is commonly observed during tolerance tests involving repeated daily topical administration to the eyes for 28 consecutive days.
No other ocular effects were observed during this study.
The administration of EXAMPLE 1 or Xalatan® did not have any macroscopic effects on the organs.
The histological analysis of both eyes (treated and untreated) did not reveal any signs of pathology, whatever the treatment.
As was the case for Xalatan®, the administration of EXAMPLE 1 did not have any microscopic ocular effects.
In conclusion, after two daily instillations of 50 μl of EXAMPLE 1 (latanoprost 0.005%) for 28 days in the right eye of pigmented rabbits, very slight ocular effects were observed, similar to the control group treated with Xalatan® 0.005% eye drops. The ocular effects observed are considered to be non-specific and essentially due to repeated daily instillations over 28 consecutive days. Consequently, under these experimental conditions, the administration of EXAMPLE 1 was tolerated very well on the macroscopic and microscopic levels, as was the case for Xalatan®.

5/CLINICAL TESTS ON THE EXAMPLE 1 COMPOSITION

5-1/Efficacy

Introduction

A 3-month exploratory, randomized, double blind, multi-center, cross-over, phase II pilot clinical study including 30 patients was designed to compare the pharmacokinetics, efficacy and safety of the EXAMPLE 1 ophthalmological preparation (latanoprost 0.005%) compared with another ophthalmological preparation also containing latanoprost at 0.005% (Xalatan®) in patients recently diagnosed with open-angle glaucoma or ocular hypertension.

The objective of this study was to compare the latanoprost single dose unit ophthalmic preparation (without preservative) and Xalatan® eye drops (benzalkonium chloride-preserved) after a 6 weeks treatment with one medication and 6 weeks with the other medication in newly diagnosed glaucomatous patients and in newly diagnosed patients with ocular hypertension.

This study was conducted according to accepted standards of Good Clinical Practice (GCP), the specific guidelines if any, and in agreement with the Declaration of Helsinki (2004) and local regulations.

Protocol

At the first visit (Visit 1), the patients were chosen at random to receive one of the 2 following treatments:
Latanoprost 0.005% formulation with a preservative (Multi-dose [MD], Xalatan®) once a day at 8 PM for 6 weeks in both eyes;
Latanoprost 0.005% formulation without preservatives (Single-dose unit [SDU], EXAMPLE 1) once a day at 8 PM for 6 weeks in both eyes.

After these 6 weeks, the subjects were exchanged and took the other study medicine (with no washout period), in other words, those who received the first formulation with the preservative received the formation without preservatives during the second period and vice-versa. The second period also lasted 6 weeks.

All patients were attended 3 visits at the investigation centre during the study: the inclusion visit (Day 0), the follow-up visit (Day 42) and the final visit (Day 84). IOP was evaluated in each eye at Day 0, Day 42 and Day 84, at 8 AM (±30 min), 12 PM (±30 min), 4 PM (±30 min) and 8 PM (±30 min) Global efficacy was also assessed by the investigator. Safety and tolerance were also evaluated both by the patients and the investigators.

Results

The results are presented in the following table:
Average IOP Obtained after Treatment with Xalatan® or Example 1

|  |  | After 6 weeks of treatment | | |
| --- | --- | --- | --- | --- |
| Mean IOP at | Baseline | Xalatan ® | EXAMPLE 1 | Xalatan ®- EXAMPLE 1 |
| 8 AM | 22.63 | 16.20 | 16.91 | −0.71 |
| 12 PM | 23.56 | 16.43 | 16.85 | −0.42 |
| 4 PM | 22.55 | 16.47 | 16.28 | 0.19 |
| 8 PM | 21.62 | 16.71 | 16.43 | 0.27 |
| Diurnal average | 22.59 | 16.45 | 16.65 | −0.20 |

The differences between mean IOP between the two products were not statistically significant whatever the timepoint. The mean diurnal IOP was reduced of 6.14 mmHg (27.2%) after 6 weeks of Xalatan therapy and of 5.94 mmHg (26.3%) after 6 weeks of EXAMPLE 1 therapy.

Efficacy in reducing IOP was therefore comparable with both treatments, with a "normal" IOP being obtained after both treatments.

Considering the measurements at the physiologic peak of IOP at 8 AM, Xalatan® had a reducing effect on IOP that was slightly better by approximately 0.7 mmHg However, this difference is not statistically significant (p=0.118).

Furthermore, this tendency decreases throughout the day and is reversed during the afternoon and evening. Thus, it illustrates the effect throughout the day of the EXAMPLE 1 formulation, already observed in the evaluation study on the IOP reduction in normotensive rats.

Consequently, the EXAMPLE 1 formulation is effective on IOP starting at 8 AM and remains just as effective throughout the day, even though it does not contain any preservatives.

In conclusion, diurnal IOPs after 6 weeks of the 2 treatments were not statistically different, with an efficacy, characterized by a so-called "normal" IOP, maintained throughout the day with the EXAMPLE 1 formulation containing no preservatives.

5-2/Safety

Introduction

The aim of this study (clinical test/phase III) was to assess the safety of EXAMPLE 1 (Latanoprost 0.005% single dose non-preserved eye drops) versus Xalatan (Latanoprost 0.005% preserved eye drops) following once daily treatment for 3 months in ocular hypertensive or glaucomatous patients.

Protocol

International, multicentre, randomised, investigator-masked, 2 parallel groups study versus reference product in 360 evaluable patients treated for 3 months. Once screening visit (D-42), one inclusion visit (D0) and 3 post-baseline visits (D15, D42, D84) were planned.

A total of 463 patients were selected, 404 patients were included and randomised and 402 took the study treatment: 213 in the EXAMPLE 1 group and 189 in the Xalatan group. In all 392 patients completed the study: 206 in the EXAMPLE 1 group and 186 in the Xalatan group.

The Safety Set was composed of 213 patients in the EXAMPLE 1 group and 189 patients in the Xalatan group. The modified Intent-to-treat (mITT) Set was composed of 353 patients: 189 in the EXAMPLE 1 group and 164 in the Xalatan group. The Per protocol (PP) Set was composed of 177 patients in the EXAMPLE 1 group and 153 in the Xalatan group.

In the Safety Set, there was no relevant difference between treatment groups for demographics and other baseline characteristics, except slightly higher rate of female patients in the EXAMPLE 1 group (53.5%) than in the Xalatan group (45.5%). Age ranged between 24 and 93 years with a mean±SD of 64.7±11.5 years.

In the Safety Set, corneal thickness at D-42 ranged between 500 and 610 μm with a mean±SD value of 542±22 μm in the EXAMPLE 1 group and of 543±22 μm in the Xalatan group.

The mean treatment duration (on average 83 days) was similar in both treatment groups. Treatment compliance based upon instillation was >98% in each treatment group.

Results

Ocular Adverse Events

Ocular adverse events (AEs) were reported in 18 (8.5%) patients in the EXAMPLE 1 group versus 22 (11.6%) in the Xalatan group. The most frequent ocular AE regardless of treatment groups was drug intolerance which was reported in 1 (0.5%) patient in the EXAMPLE 1 group versus 4 (2.1%) patients in the Xalatan group. There was one severe ocular discomfort reported in the EXAMPLE 1 group and most other ocular AEs were of mild or moderate intensity.

Ocular AEs with a relationship with the study drug were reported in 8 (3.8%) patients in the EXAMPLE 1 group (including 1 patient with 1 moderate photophobia, and 1 patient with 1 mild optic disc haemorrhage, for which the relationship could not be assessed) versus 10 (5.3%) patients in the Xalatan group.

The study drug was withdrawn due to an ocular AE in 2 patients from the EXAMPLE 1 group (1 moderate drug intolerance on D7 and 1 moderate eye pruritus on D28) and in 1 patient in the Xalatan group (1 moderate allergic conjunctivitis on D9). All ocular AEs causing drug withdrawal were related to the study drug according to the investigator. All patients recovered when drug was withdrawn. No serious ocular AE was reported in this study.

Systemic Adverse Events

Systemic AEs were reported in 28 (13.1%) patients in the EXAMPLE 1 group versus 32 (16.9%) in the Xalatan group. None of the systemic AEs were related to the study drug in the EXAMPLE 1 group while 6 AEs reported in 4 (2.1%) patients in the Xalatan group were considered by the investigator as related to treatment (2 headaches in the same patient, 1 dizziness, 1 migraine, and 1 palpitation and 1 muscular weakness). All were of mild intensity. One major depression in the EXAMPLE 1 group and one mild migraine in the Xalatan group led to study drug withdrawal. Six patients had a systemic serious AEs (SAEs): 5 patients in the EXAMPLE 1 group (1 tibia fracture, 1 major depression, 1 syncope, 1 chest pain, and 1 fibula fracture and 1 patient in the Xalatan group (1 renal colic). None had a relationship with treatment according to the investigator.

Subjective Symptoms Upon Instillation

Overall, the ocular subjective symptoms score upon instillation (pruritus, burning/stinging, sticky eye, eye dryness sensation, foreign body sensation) were significantly less frequent in the EXAMPLE 1 group than in the Xalatan group on D42 (p=0.001) and D84 (p=0.001) (see table below). This was primarily due to burning/stinging: 5.2% vs. 14.0% on D15 (p=0.004), 6.8% vs. 15.1% on D42 (p=0.006), and 7.3% vs. 19.9% on D84 (p<0.001) and to pruritus (1.5% vs. 5.4% on D42 and 2.4% vs. 6.0% on D84).

| Total subjective ocular symptom scores upon instillation at each visit (Safety Set) | | | |
|---|---|---|---|
| Visit | | EXAMPLE 1 | Xalatan | P value* |
| D15 | n | 209 | 186 | |
| | Mean ± SD | 0.25 ± 0.81 | 0.40 ± 0.89 | 0.085 |
| | 95% CI | [0.14; 0.36] | [0.27; 0.53] | |
| D42 | n | 208 | 186 | |
| | Mean ± SD | 0.15 ± 0.51 | 0.41 ± 1.03 | 0.001 |
| | 95% CI | [0.08; 0.22] | [0.26; 0.56] | |
| D84 | n | 206 | 186 | |
| | Mean ± SD | 0.18 ± 0.66 | 0.46 ± 1.05 | 0.001 |
| | 95% CI | [0.09; 0.27] | [0.31; 0.61] | |

*ANOVA adjusted for country

Figure 2A:
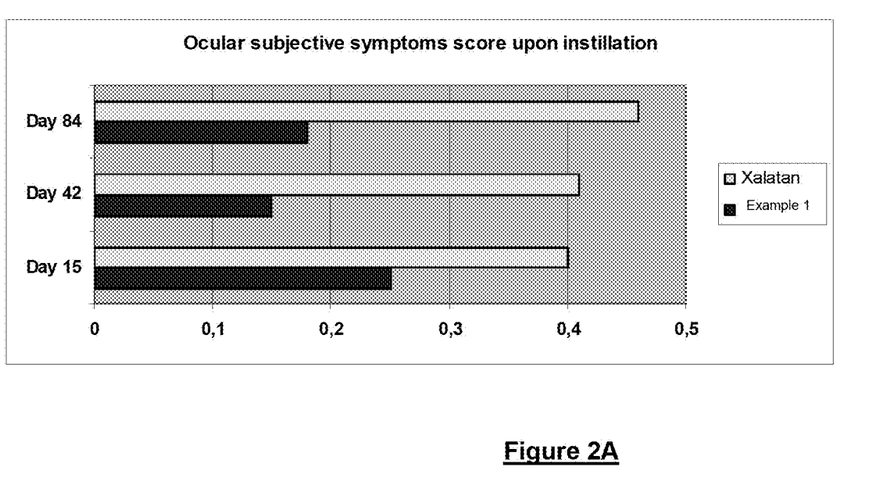

The corresponding results are shown on FIG. 2A.

Subjective Symptoms not Upon Instillation

Overall, there was a trend for less ocular subjective symptoms not upon instillation in the worse eye in the EXAMPLE 1 group compared to the Xalatan group on D42 (0.47±1.19 vs. 0.65±1.54, p=0.057), and on D84 (0.47±1.37 vs. 0.69±1.73, p=0.053). Similar results were shown for the contralateral eyes.

Figure 2B:
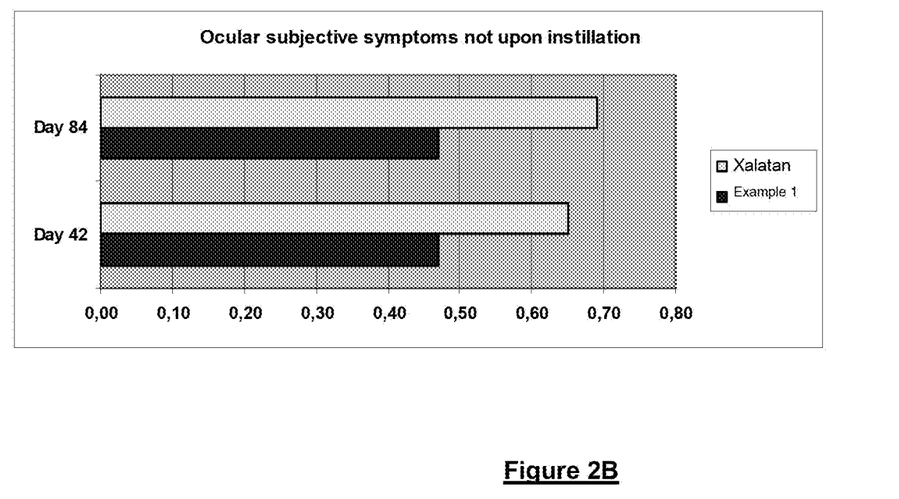

Both in the worse and contralateral eyes, irritation/burning/stinging not upon instillation were less frequent in the EXAMPLE 1 group than in the Xalatan group on D42 (7.2% vs. 13.4%) and on D84 (6.8% vs. 12.9%) in the worse eye. The corresponding results are shown on FIG. 2B.

Although the differences were not consistently statistically significant, there is a trend in favour of EXAMPLE 1 which confirms what is already observed for symptoms upon instillation.

Slit Lamp Examination

Figure 2C:
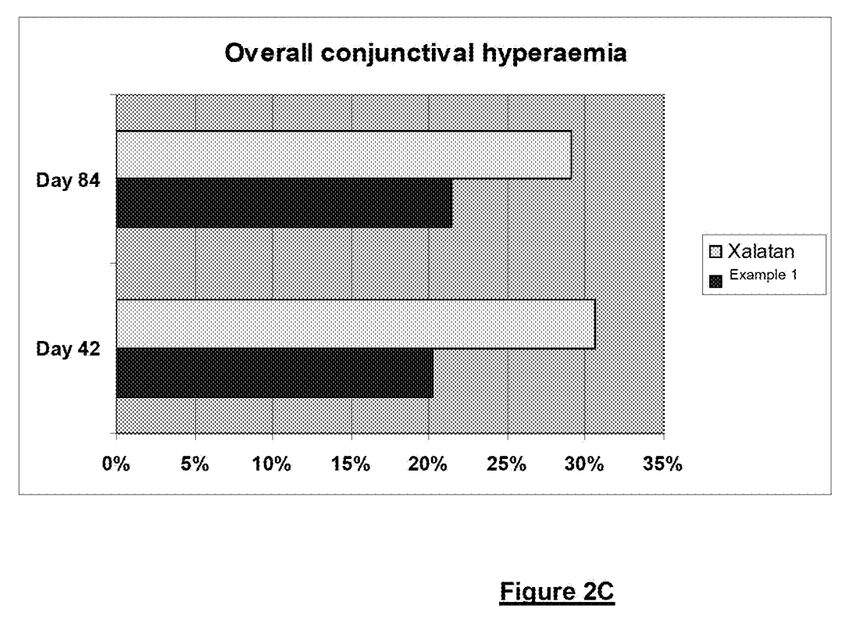

Overall conjunctival hyperaemia was less frequent in the EXAMPLE 1 group than in the Xalatan group in the worse eye with a significantly lower incidence in the EXAMPLE 1 group than in the Xalatan group on D42 (20.2% vs. 30.6%, p=0.003) and on D84 (21.4% vs. 29.1%, p=0.019). The corresponding results are shown on FIG. 2C. For other examination no difference between treatment was shown.

Global Assessment by the Investigator and by the Patient

According to the investigator, the tolerance was very satisfactory or satisfactory for more than 97% of patients in both treatment groups. However, the rate of very satisfactory tolerance was higher in the EXAMPLE 1 group than in the Xalatan group on D15 (65.1% vs. 59.7%), on D42 (74.0% vs. 65.1%) and on D84 (71.4% vs. 62.9%). Considering all assessments significant differences were found between the two treatment groups for D42 (p=0.013) and D84 (p=0.047). The D15 results failed to reach statistical significance.

At D42 and D84, more than 99% of patients in the EXAMPLE 1 group and more than 96% of patients in the Xalatan group felt the treatment to be convenient.

Altogether, the safety results suggest a better local tolerability of EXAMPLE 1 over Xalatan with less subjective symptoms upon instillation (in particular pruritus, and burning/stinging), and less hyperaemia. The tolerance was rated more frequently "very satisfactory" in patients treated with EXAMPLE 1.

In conclusion, this study demonstrates that the local tolerability for EXAMPLE 1 appeared to be better than for Xalatan, with at least the same efficacy on Intra ocular Pressure.

The invention claimed is:

1. An ophthalmic solution consisting of:
    about 0.005% (w/v) of latanoprost;
    about 5% (w/v) of macrogol glycerol hydroxystearate 40;
    about 0.1% (w/v) of carbomer 974P;
    about 0.05% (w/v) of sodium EDTA;
    about 1% (w/v) of PEG 4000;
    about 3.5% (w/v) of sorbitol;
    sodium hydroxide; and
    water; wherein the ophthalmic solution has a pH of about 7.0.

2. The solution of claim 1, wherein the solution has a Brookfield viscosity at 25° C. between 8 and 20 mPa·s.

3. A method for treating open-angle glaucoma or reducing intraocular pressure comprising administration of a solution of claim 1 to an individual in need thereof.

4. The method of claim 3, comprising topically administering one drop of the solution of claim 1 a day to each eye in humans or animals.

5. Single-use or multi-dose bottle made of LDPE containing no additives containing the ophthalmic solution covered by claim 1.

* * * * *